United States Patent
Alshareef et al.

(10) Patent No.: US 11,617,558 B2
(45) Date of Patent: Apr. 4, 2023

(54) MULTIMODAL STRAIN SENSOR AND METHOD

(71) Applicant: KING ABDULLAH UNIVERSITY OF SCIENCE AND TECHNOLOGY, Thuwal (SA)

(72) Inventors: Husam Niman Alshareef, Garland, TX (US); Kang Hyuck Lee, Thuwal (SA); Yizhou Zhang, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 507 days.

(21) Appl. No.: 16/765,081

(22) PCT Filed: Nov. 28, 2018

(86) PCT No.: PCT/IB2018/059426
§ 371 (c)(1),
(2) Date: May 18, 2020

(87) PCT Pub. No.: WO2019/116135
PCT Pub. Date: Jun. 20, 2019

(65) Prior Publication Data
US 2021/0219939 A1    Jul. 22, 2021

Related U.S. Application Data (60) Provisional application No. 62/649,211, filed on Mar. 28, 2018, provisional application No. 62/597,470, filed on Dec. 12, 2017.

(51) Int. Cl.
*A61B 7/00* (2006.01)
*A61B 5/00* (2006.01)
(Continued)

(52) U.S. Cl.
CPC ................ *A61B 7/00* (2013.01); *A61B 5/683* (2013.01); *C08J 3/075* (2013.01); *C08K 3/14* (2013.01);
(Continued)

(58) Field of Classification Search
CPC ...................................... A61B 5/683
(Continued)

(56) References Cited

U.S. PATENT DOCUMENTS 10,381,143 B2 * 8/2019 Khoshkava ......... H01F 27/2828
2005/0274454 A1 * 12/2005 Extrand .................. C09J 11/04
428/323
(Continued)

FOREIGN PATENT DOCUMENTS

| CN | 107029562 A | 8/2017 |
|---|---|---|
| EP | 3279247 A1 | 2/2018 |

OTHER PUBLICATIONS

Boland, C.S., et al., "Sensitive Electromechanical Sensors Using Viscoelastic Graphene-Polymer Nanocomposites," Science, Dec. 9, 2016, vol. 354, Issue 6317, pp. 1257-1260.
(Continued)

*Primary Examiner* — George B Bennett
(74) *Attorney, Agent, or Firm* — Patent Portfolio Builders PLLC (57) ABSTRACT

There is a viscoelastic strain sensor that includes a sensing layer including a viscoelastic material, the viscoelastic material including a viscoelastic hydrogel and a conductive nanofiller. The viscoelastic material has a fractional resistance change that increases with an increase of an applied tensile strain, and the viscoelastic material has a fractional resistance change that decreases with an applied compressional strain.

24 Claims, 12 Drawing Sheets

(51) Int. Cl.
| | |
|---|---|
| *C08J 3/075* | (2006.01) |
| *C08K 3/14* | (2006.01) |
| *C08K 3/28* | (2006.01) |
| *C08K 7/00* | (2006.01) |
| *G01L 1/22* | (2006.01) |
| *G01B 7/16* | (2006.01) |
| *G01B 1/00* | (2006.01) |

(52) U.S. Cl.
CPC ............... *C08K 3/28* (2013.01); *C08K 7/00* (2013.01); *G01B 1/00* (2013.01); *G01B 7/18* (2013.01); *G01L 1/2287* (2013.01); *A61B 5/6814* (2013.01); *A61B 5/6822* (2013.01); *A61B 5/6825* (2013.01); *A61B 2562/0204* (2013.01); *A61B 2562/0261* (2013.01); *A61B 2562/0285* (2013.01); *A61B 2562/164* (2013.01); *C08K 2201/001* (2013.01); *C08K 2201/011* (2013.01); *G01B 7/16* (2013.01); *G01N 2203/0069* (2013.01); *G01N 2203/0094* (2013.01)

(58) Field of Classification Search
USPC .......................................................... 33/512
See application file for complete search history.

(56) References Cited

U.S. PATENT DOCUMENTS

| | | | |
|---|---|---|---|
| 2009/0171406 A1* | 7/2009 | Foley ................... | A61N 1/05 607/116 |
| 2015/0259212 A1 | 9/2015 | Li et al. | |
| 2019/0106544 A1* | 4/2019 | Bao ..................... | B29C 73/28 |
| 2021/0113099 A1* | 4/2021 | Rogers ................ | A61B 5/4803 |
| 2021/0219939 A1* | 7/2021 | Alshareef .......... | A61B 5/02438 |
| 2022/0323006 A1* | 10/2022 | Conia ................... | A61B 5/686 |
| 2022/0346713 A1* | 11/2022 | Lefler ................... | A61B 5/685 |

OTHER PUBLICATIONS

Cai, G., et al., "Extremely Stretchable Strain Sensors Based on Conductive Self-Healing Dynamic Cross-Links Hydrogels for Human-Motion Detection," Advanced Science, Sep. 7, 2016, vol. 4, No. 2, pp. 1600190 (7 pages).

Cai, Y., et al., "Stretchable Ti3C2Tx MXene/Carbon Nanotube Composite Based Strain Sensor with Ultrahigh Sensitivity and Tunable Sensing Range," ACS Nano, Dec. 4, 2017, vol. 12, No. 1, pp. 56-62.

Cao, J., et al., "Multiple Hydrogen Bonding Enables the Self-Healing of Sensors for Human-Machine Interactions," Angewandte Chemie International Edition, May 23, 2017, vol. 56, pp. 8795-8800.

Chen, S., et al., "A Highly Stretchable Strain Sensor Based on a Graphene/Silver Nanoparticle Synergic Conductive Network and a Sandwich Structure," Journal of Materials Chemistry C, Apr. 1, 2016, vol. 4, pp. 4304-4311.

Database WPI, Week 201761, Thomson Scientific, Longon, GB, AN 2017-56462A (3 pages) (Referred to with CN 107029562 in ISR).

Hassan, C.M., et al., "Structure and Applications of Poly(vinyl alcohol) Hydrogels Produced by Conventional Crosslinking or by Freezing/Thawing Methods," Advances in Polymer Science, Oct. 20, 2000, pp. 37-65.

Hong, S. Y., et al., "Stretchable Active Matrix Temperature Sensor Array of Polyaniline Nanofibers for Electronic Skin," Advanced Materials, Dec. 2, 2015, vol. 28, pp. 930-935.

Hu, M., et al., "All-Solid-State Flexible Fiber-Based MXene Supercapacitors," Advanced Materials Technologies, Aug. 21, 2017, vol. 2, No. 10, pp. 1700143 (6 pages).

International Search Report in corresponding/related International Application No. PCT/IB2018/059426, dated Mar. 4, 2019.

Lin, Y., et al., "A Highly Stretchable and Sensitive Strain Sensor Based on Graphene-Elastomer Composites with a Novel Double-Interconnected Network," Journal of Materials Chemistry C, Jun. 7, 2016, vol. 4, pp. 6345-6352.

Shi, J., et al., "Graphene Welded Carbon Nanotube Crossbars for Biaxial Strain Sensors," Carbon, Aug. 7, 2017, vol. 123, pp. 786-793.

Shu, L., et al., "A New Approach for Readout of Resistive Sensor Arrays for Wearable Electronic Applications," IEEE Sensors Journal, Jan. 2015, vol. 15, pp. 442-452.

Tang, Y., et al., "Highly Stretchable and Ultrasensitive Strain Sensor Based on Reduced Graphene Oxide Microtubes-Elastomer Composite," Applied Materials & Interfaces, Nov. 23, 2015, vol. 7, pp. 27432-27439.

Wang, B., et al., "Graphene/Polydimethylsiloxane Nanocomposite Strain Sensor," Review of Scientific Instruments, Oct. 23, 2013, vol. 84, pp. 105005-1 105005-4.

Woo, S.-J., et al., "A Thin All-Elastomeric Capacitive Pressure Sensor Array Based on Micro-Contact Printed Elastic Conductors," Journal of Materials Chemistry C, Mar. 25, 2014, vol. 2, pp. 4415-4422.

Written Opinion of the International Searching Authority in corresponding/related International Application No. PCT/IB2018/059426, dated Mar. 4, 2019.

Wu, X., et al., "Highly Sensitive, Stretchable, and Wash-Durable Strain Sensor Based on Ultrathin Conductive Layer@Polyurethane Yarn for Tiny Motion Monitoring," Applied Materials & Interfaces, Mar. 31, 2016, vol. 8, pp. 9936-9945.

Zhang, Y.-Z., et al., "MX enes Stretch Hydrogel Sensor Performance to New Limits," Science Advances, Jun. 15, 2018, 7 pages.

* cited by examiner

MULTIMODAL STRAIN SENSOR AND METHOD

CROSS-REFERENCE TO RELATED APPLICATIONS

This application is a U.S. National Stage Application of International Application No. PCT/IB62018/059426, filed on Nov. 28, 2018, which claims priority to U.S. Provisional Patent Application No. 62/597,470, filed on Dec. 12, 2017, entitled "HIGHLY STRETCHABLE AND SELF-HEALABLE MULTIMODAL STRAIN SENSOR BASED ON VISCOELASTIC HYDROGEL COMPOSITE," and U.S. Provisional Patent Application No. 62/649,211, filed on Mar. 28, 2018, entitled "MULTIMODAL STRAIN SENSOR AND METHOD," the disclosures of which are incorporated herein by reference in their entirety.

BACKGROUND

Technical Field

Embodiments of the subject matter disclosed herein generally relate to methods and strain sensors, and more specifically, to multimodal strain sensors based on viscoelastic polymer composite materials.

Discussion of the Background

Figure 1A:
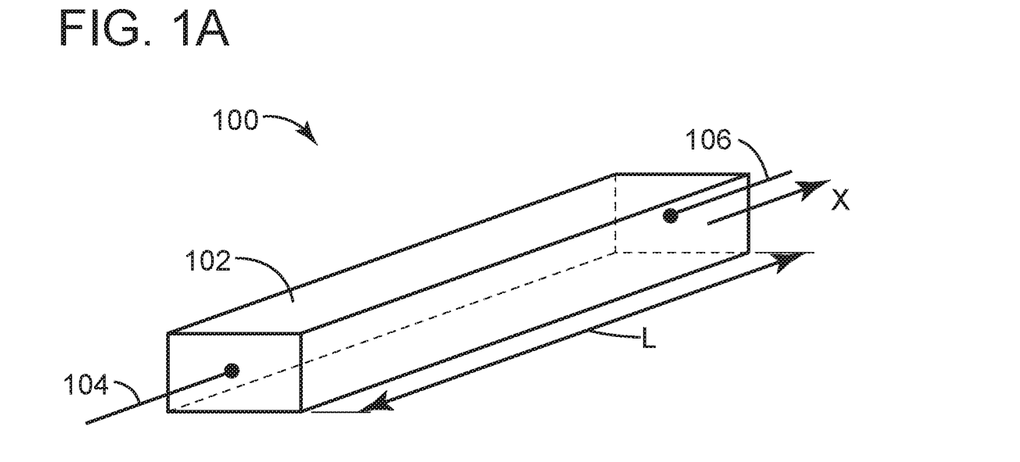
FIGS. 1A and 1B illustrate a traditional strain sensor.
Figure 1B:
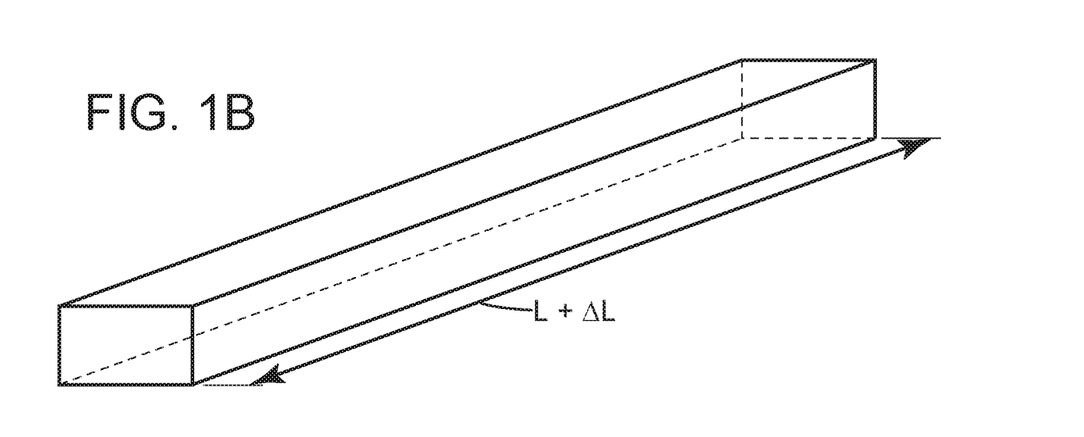

The sensing mechanism of conventional resistive strain sensors (or strain gauges) is due to the conductance change of an electrical conductor caused by geometrical deformation. FIG. 1A shows such a traditional strain sensor 100 having a conductor body 102 that extends along an axis X. Two leads 104 and 106 are connected to the ends of the body 102. These leads are traditionally connected to a Wheatstone bridge for determining a change in the conductance of the body 102. When the electrical conductor 100 is stretched as shown in FIG. 1B, it will become narrower and longer, increasing its end-to-end electrical resistance. Conversely, when the electrical conductor is compressed, it will become broader and shorter, decreasing its end-to-end electrical resistance. The Wheatstone bridge (or an equivalent device) is capable to measure these changes. These changes are proportional with the strain that is applied to the conductor. Thus, by knowing the value of the conductance change, one can calculate the applied strain.

Recently, a special class of conductive network structures, whose geometry and conductivity can both be changed by deformations, has been used to improve the sensitivity of strain sensors (see, for example, Wang et al., Rev. Sci. Instrum. 84, (2013) 105005, Lin et al., J. Mater. Chem. C, 4, (2016) 6345-6352, Tang et al., ACS Appl. Mater. Interfaces 7, (2015) 27432-27439, and Boland et al., Science 354, (2016) 1257-1260).

However, although these strain sensors have great strain sensitivity, they can only detect strains that are parallel to the direction of the electric current. Therefore, more than four electrodes are required to sense complex motions of the target object.

Thus, there is a need for a new material that has a very good strain sensitivity and is also capable of detecting complex motions with a limited number of electrodes, to overcome the problems of the existing strain sensors discussed above.

SUMMARY

According to an embodiment, there is a viscoelastic strain sensor that includes a sensing layer including a viscoelastic material. The viscoelastic material includes a viscoelastic hydrogel and a conductive nanofiller. The viscoelastic material has a fractional resistance change that increases with an increase of an applied tensile strain. The viscoelastic material has a fractional resistance change that decreases with an applied compressional strain.

According to another embodiment, there is a method for determining a strain with a strain sensor. The method includes providing a sensing layer of the strain sensor, applying the strain to the sensing layer, measuring a fractional resistance change of the sensing layer due to the applied strain, and transforming the measured fractional resistance change into a feature that characterizes the applied strain. The sensing layer includes a viscoelastic hydrogel and a conductive nanofiller. The viscoelastic material has the fractional resistance change that increases with an increase of an applied tensile strain, and the viscoelastic material has a fractional resistance change that decreases with an applied compressional strain.

According to still another embodiment, there is a viscoelastic material that includes a viscoelastic hydrogel and a conductive nanofiller. The viscoelastic material has a fractional resistance change that increases with an increase of an applied tensile strain, and the fractional resistance change decreases with an applied compressional strain.

BRIEF DESCRIPTION OF THE DRAWINGS

The accompanying drawings, which are incorporated in and constitute a part of the specification, illustrate one or more embodiments and, together with the description, explain these embodiments. In the drawings:

FIGS. 11A to 110 illustrate the poor response of a hydrogel when used to recognize the sounds;

DETAILED DESCRIPTION

The following description of the embodiments refers to the accompanying drawings. The same reference numbers in different drawings identify the same or similar elements. The following detailed description does not limit the invention.

Instead, the scope of the invention is defined by the appended claims. The following embodiments are discussed, for simplicity, with regard to a polymer composite material called herein M-hydrogel. However, the invention is not limited to this material, but it may be used with other polymer composite materials.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 2A:
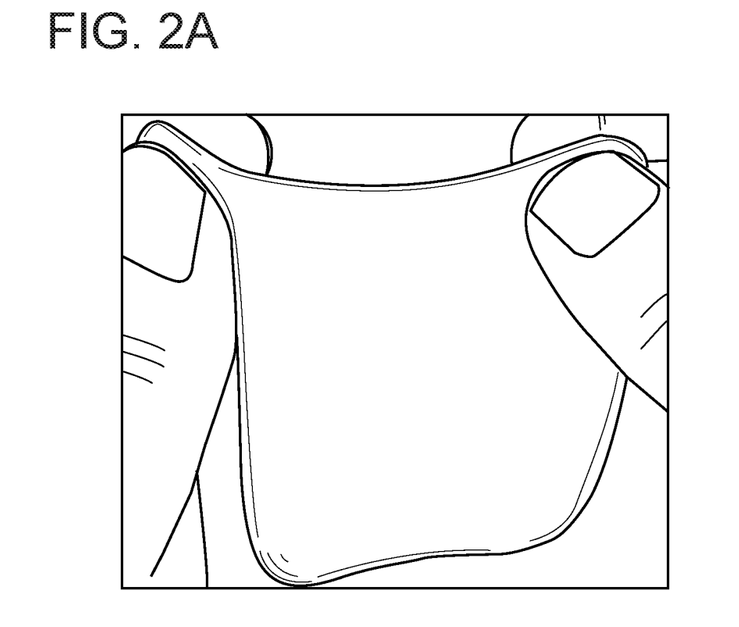
FIGS. 2A and 2B illustrate a polymer composite material having high stretchability.
Figure 2B:
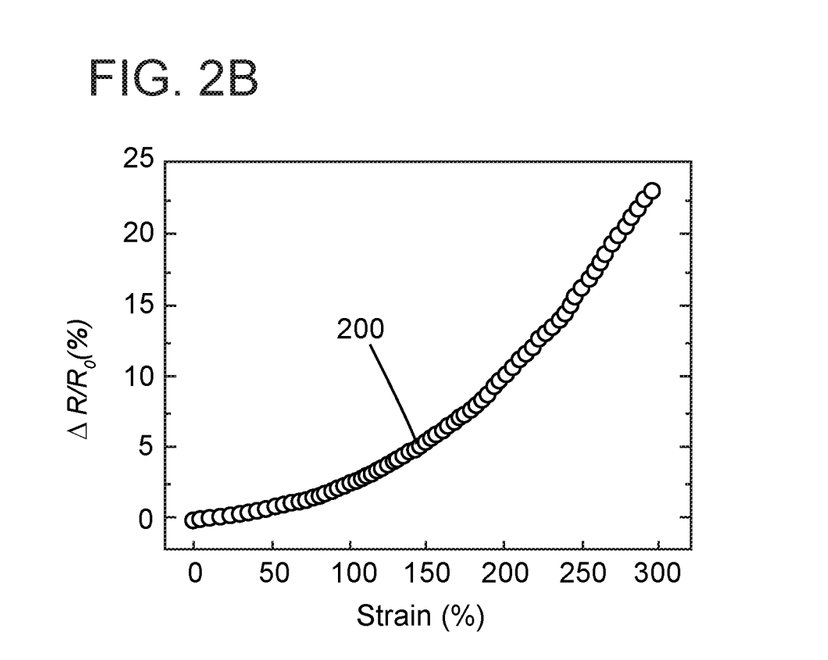

According to an embodiment, a novel polymer composite material is used as the body of the strain sensor. The novel polymer composite material is very malleable as illustrated in FIG. 2A. When strain is applied to the novel polymer composite, its fractional resistance change (henceforth referred to as $\Delta R/R0$, where R0 is the resistance of the sensing material without strain and $\Delta R$ is the amount of resistance change after applying strain) curve 200 as a function of the applied strain (%) shows a typical behavior similar to conventional resistive strain sensors as illustrated in FIG. 2B. This means that the new polymer composite material can be used for all the typical strain sensor applications.

Moreover, the new polymer composite material can fit arbitrary surfaces with complex shapes such as human skin near the joints, or it can fully cover the tiny spaces between wrinkles due to the sticky and easy shape-transformable characteristics of its components.

According to an embodiment, the novel polymer composite material includes (1) a viscoelastic hydrogel and (2) conductive nanofillers. The hydrogel is a class of viscoelastic materials composed of three-dimensional (3D) networks of hydrophilic polymers crosslinked, chemically or physically, with the capacity to absorb and retain a large amount of water (up to 90%). The hydrogel may include natural or synthetic polymeric networks. The hydrogels also possess a degree of flexibility very similar to natural tissue, due to their significant water content. The term "viscoelastic" is understood herein to be a property of materials to exhibit both viscous and elastic characteristics when undergoing deformation. Viscous materials resist shear flow and strain linearly with time when a stress is applied. Elastic materials strain when stretched and quickly return to their original state once the stress is removed. Viscoelastic materials have elements of both of these properties and, as such, exhibit time-dependent strain.

Conductive hydrogels are potential candidates for electromechanical sensing materials for applications such as wearable electronics, soft robotics and prosthetics, which require the sensors to be highly sensitive, stretchable, and easily adhere to arbitrary and complex surfaces, such as human skin. However, hydrogel based electro-mechanical sensors generally exhibit relatively low sensitivity. Furthermore, as viscoelastic materials, their electro-mechanical responses to external forces show unstable noises with hysteresis and fluctuation due to the unexpected viscous deformations.

Recently, a special class of conductive nanofillers, whose geometry and conductivity can both be changed by deformations, have been used to improve the sensitivity of composite strain sensors (see, for example, Wang et al., Rev. Sci. Instrum. 84, (2013) 105005, Lin et al., J. Mater. Chem. C, 4, (2016) 6345-6352, Tang et al., ACS Appl. Mater. Interfaces 7, (2015) 27432-27439, and Boland et al., Science 354, (2016) 1257-1260). Although these nanofiller networks can greatly improve sensitivity, they still cannot overcome the limitations originated from viscous deformations. In addition, these nanofillers usually cannot maintain their deformed network structure caused by viscous deformations, due to their easy motion within the hydrogel matrix and possible rearrangement of the network structure by an electric field. As a result, their sensing reliability is compromised.

The inventors of the present application have realized that MXenes, a class of two-dimensional (2D) early transition metal carbides and/or carbonitrides and/or nitrides, might cure the problems noted in the above nanofillers. These materials consist of few atoms thick layers of transition metal carbides, nitrides or carbonitrides. More specifically, a MXenes includes (1) a transition metal M and (2) atom X, which can be C or N based. The MXenes may also include a functional group T, which may include O, F or OH. The MXenes may be generically represented as $M_{n+1}X_n$, when n is 1, 2 or 3. MXenes combine the metallic conductivity of the transition metal carbides and hydrophilic nature because of their hydroxyl or oxygen terminated surface.

The MXenes may be prepared by selectively etching out the element "A" from the three-dimensional (3D) structured ceramic known as MAX. Similar to graphene, these 2D laminated nanocrystals exhibit large specific surface area, high electrical conductivity, favorable mechanical strength and other interesting characteristics. Owing to the abundant surface function groups T (OH, O, F, H, etc.), MXenes show good hydrophilicity. Because of the multiple active sites on the surface, MXenes can be used as active materials for catalysis, electrochemical energy storage, etc.

Figure 3:
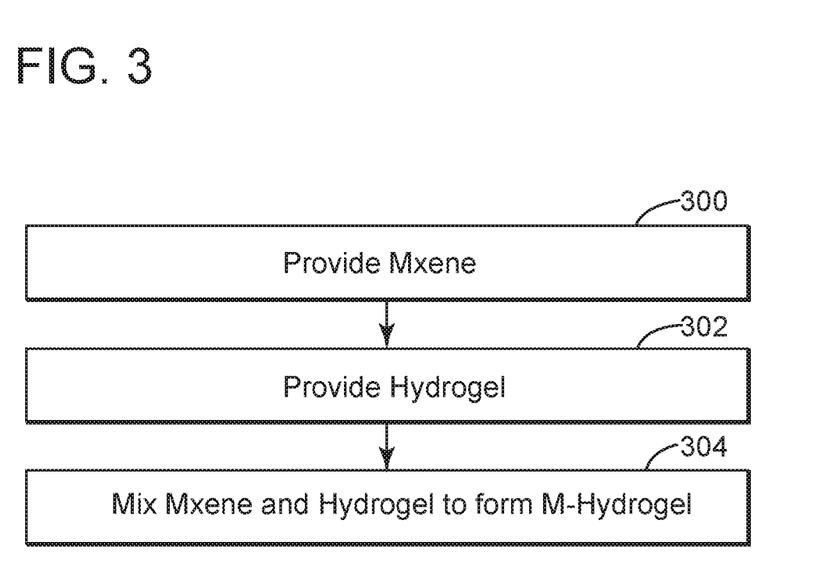
FIG. 3 is a flowchart of a method for obtaining a polymer composite material.

According to an embodiment, a method for preparing MXene based hydrogel (called M-hydrogel in here) is now discussed with regard to FIG. 3. Note that the M-hydrogel now discussed is only one possible implementation of the novel polymer composite material discussed above. In step 300, MXene ($Ti_3C_2$) nanosheets are provided in a mixing bowl. In step 302, a commercial low-cost hydrogel ("crystal clay," which is composed of Poly (vinyl alcohol), water and anti-dehydration additives) is also provided in the mixing bowl. In step 304, the two components are mixed together to form the M-hydrogel. In one application, the nanosheets are randomly distributed inside the hydrogel. The concentration of the Mxene by mass weight may be larger than zero and smaller than 10%. The resulting M-hydrogel shows extremely high stretchability, which is much higher than the pristine hydrogel and malleability. These properties are attributed to the abundant hydrophilic surface functional groups such as —F and —OH on MXene nanosheets, which form strong hydrogen bonds between the MXene nanosheets and the hydrogel matrix.

Thus, unlike traditional hydrogels using other conductive fillers, the M-hydrogels is "softer" and more stretchable than the pristine hydrogel. The strong hydrogen bonding and the half-liquid property of hydrogel also endow the M-hydrogel with instantaneous self-healability (i.e., the object can restore its original properties after plastic and/or viscous deformations), and an excellent conformability and adhesiveness to various surfaces including the human skin.

It was observed that the addition of MXene nanosheets to the hydrogel may significantly improve the tensile strain sensitivity of the hydrogel, e.g., 5 times increase at 4.1 wt % of the MXene nanosheets. At the same time, the hydrogel shows a much higher sensitivity under compressive strains.

Figure 4A:
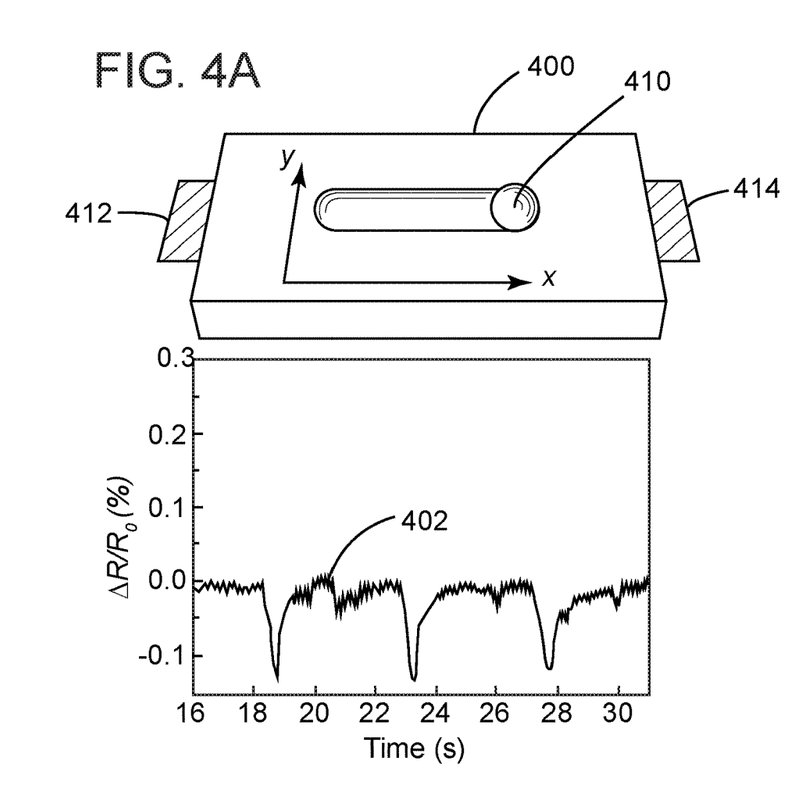
FIGS. 4A and 4B illustrate motion sensing capabilities of the polymer composite material.
Figure 4B:
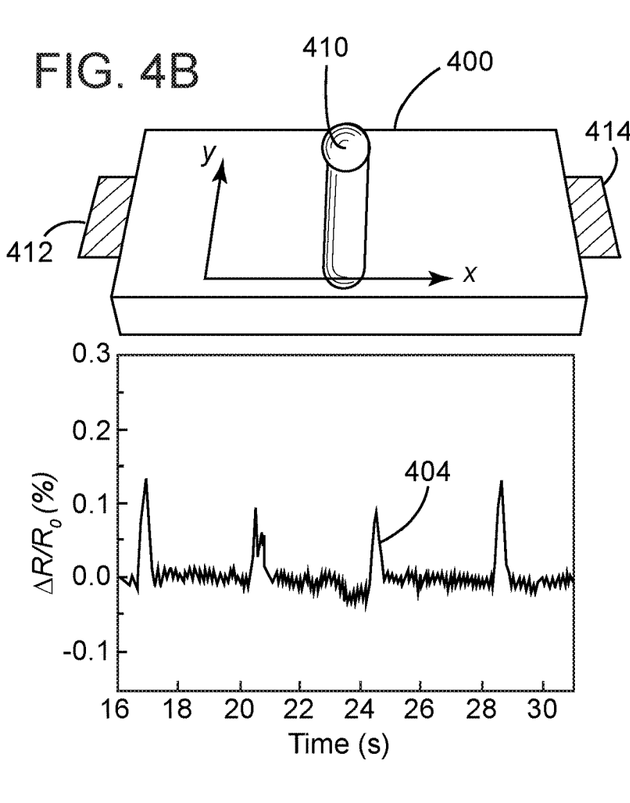

For example, as shown in FIGS. 4A and 4B, a strain sensor 400 having a body that includes the M-hydrogel material exhibits different responses 402 and 404 (in terms of the change in resistance over time) when a strain exerted by a ball 410 is applied along the X axis or the Y axis. Metallic pads 412 and 414 are used to connect the sensor to a measuring device for measuring the change in resistance.

Based on this feature of the M-hydrogel, both the direction and speed of motions can be detected conveniently by using the M-hydrogel without complex circuit design. These unique sensing characteristics of the M-hydrogel are used in a strain sensor to add extra dimensions to the sensing capability.

Figure 5A:
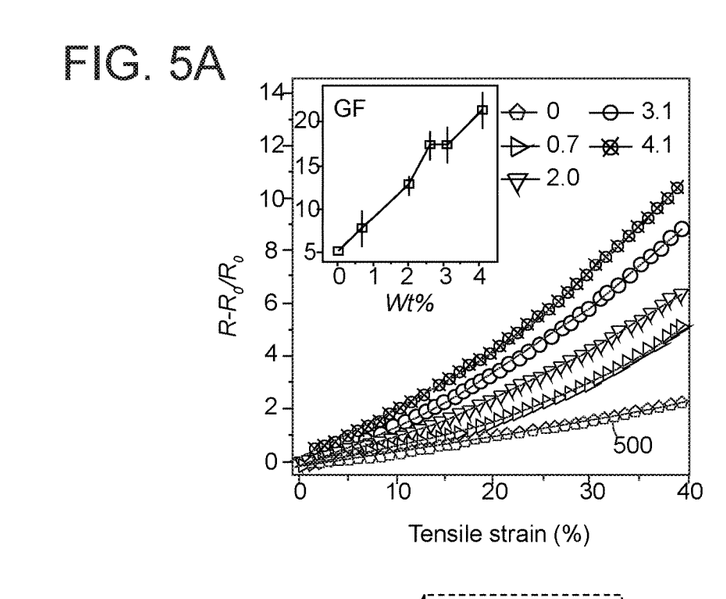
FIGS. 5A and 5B illustrate the fractional resistance change of the polymer composite material when exposed to a tensile strain and a compressive strain.
Figure 5B:
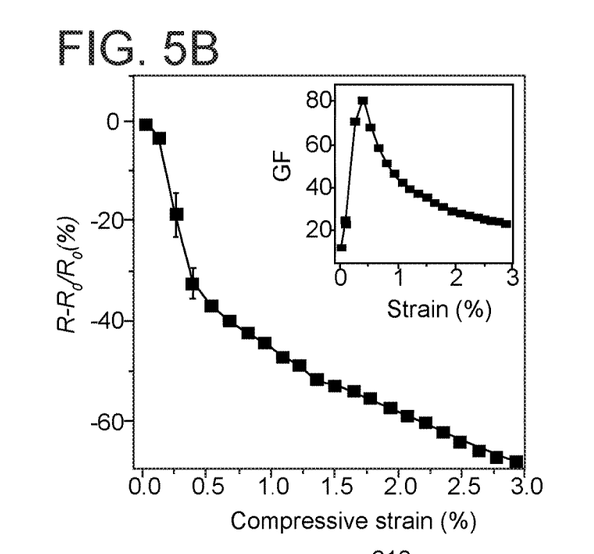

The electro-mechanical responses of the M-hydrogel to tensile and compressive deformation were characterized as illustrated in FIGS. 5A and 5B. Under tensile deformation, the resistance increases, and the fractional resistance change $(R-R_0/R_0)$ of M-hydrogel heightens with increasing strain (see FIG. 5A for MXene weight percentages of 0, 0.7, 2.0, 3.1 and 4.1). In one application, the fractional resistance change $(R-R_0/R_0)$ of the M-hydrogel increases in a nonlinear fashion with increasing the strain (see FIG. 5A for MXene weight percentages of 0, 0.7, 2.0, 3.1 and 4.1)), unlike pristine hydrogel whose fractional resistance change follows a linear relationship 500 with strain. The relation between the change in resistance of the M-hydrogel and the applied tensile deformation demonstrates the unique role of MXene in the composite hydrogel material. Thus, the M-hydrogel (viscoelastic material) shows asymmetrical sensitivity between compressive and tensile strain, which makes it capable of detecting both the direction and speed of motions on a sensing layer having such material.

For example, the fractional resistance change under compressive strains is much higher than under tensile strains. This asymmetrical strain sensitivity coupled with viscous deformation (self-recoverable residual deformation) is exploited to add new dimensions to the sensing capability of hydrogels. Consequently, both the direction and speed of motions on the hydrogel surface can be detected conveniently. Moreover, due to this unsymmetrical strain sensitivity and viscous deformations (self-recoverable residual deformation), an M-hydrogel sensor shows different resistance dependence patterns for a series of deformations formed when an object moves on its surface.

Moreover, the sensitivity of the M-hydrogel to the applied tensile deformation, which is defined as the gauge factor $(GF=\Delta R/R_0 \cdot \varepsilon)$, is shown to increase from 5 to 25, as the MXene weight percentage increases from 0 to 4.1% (see inset of FIG. 5A). This sensitivity is comparable with existent strain sensors based on polymer composites, and higher than other PVA (polyvinyl acetate) hydrogel based strain sensors.

Unlike the tensile case, the fractional resistance change of the M-hydrogel decreases under an increased compressive strain as illustrated in FIG. 5B. The corresponding gauge factor GF first increases (see inset of FIG. 5B) from 12 to 80 in the compressive strain range of 0~0.5%, and then it decreases from 80 to 21 in the strain range of 0.5%~3%. This behavior has a similar trend and comparable GF value (94.8 at 0.82% strain) as the MXene thin film based piezo resistive sensors, due to the reducing of contact resistance between MXene interlayers induced by compression.

Figure 6A:
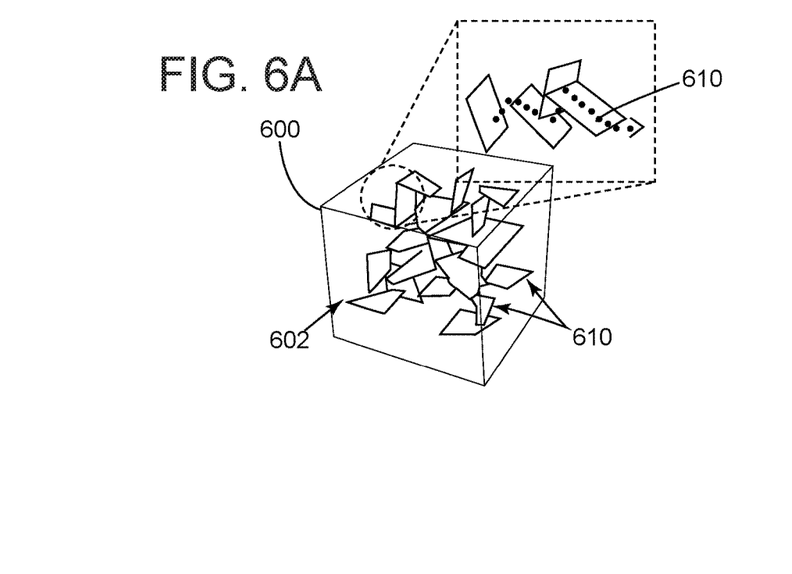
FIGS. 6A and 6B illustrate a composition of the polymer composite material and its response to applied strain.
Figure 6B:
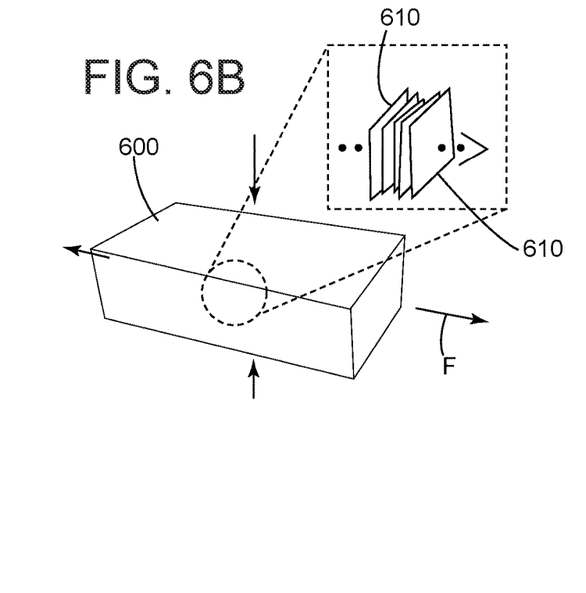

The different electromechanical properties under tensile and compressive deformation are attributed to the 3D networked structure of the MXene nanosheets within the hydrogel matrix as illustrated in FIGS. 6A and 6B. In this regard, it is noted that under tensile deformation, the resistance increases due to (a) the geometry of the M-hydrogel, which becomes narrower and longer, and (b) the decrease of interconnections between MXene nanosheets in the hydrogel matrix. Under compressive deformation, however, the geometry becomes broader and shorter, the interconnections between MXene nanosheets also increase, both effects contributing to the decrease of resistance.

Moreover, as shown in FIG. 6A, within the viscoelastic material 600, which includes the hydrogel 602, most MXene nanosheets 610 adopt the face-to-edge interconnection. This means that an edge of one nanosheet 610 contacts a face of another nanosheet. However, when the compression strain F is applied, it not only increases the interconnection points between the nanosheets, but also changes the face-edge interconnections to face-face interconnections, as illustrated in FIG. 6B. FIG. 6B shows plural nanosheets 610 being parallel to each other. By increasing the compressive strain F, the gaps between the face-to-face interconnected MXene nanosheets may be further reduced. Due to the above mentioned reasons, the compressive deformation has a larger impact on the resistance of the hydrogel than the tensile deformation. This asymmetrical strain sensitivity coupled with viscous deformation (self-recoverable residual deformation) is exploited to add new dimensions to the sensing capability of hydrogels. Consequently, both the direction and speed of motions on the hydrogel surface can be detected conveniently.

The resistance change of the M-hydrogel when the spherical object 410 in FIG. 4A (for example, object 410 may have a radius of about 1.5 mm and a weight of about 3.48 g) moves along the surface of the M-hydrogel sensor is now discussed. FIG. 4A shows the direction of the electric current as x-axis and the direction perpendicular to the electric current on the M-hydrogel surface as the y-axis. Interestingly, the resistance 402 decreased when the object 410 moved in the x direction of the M-hydrogel sensor 400, as illustrated in FIG. 4A. Conversely, the resistance 404 increased when the object 410 moved in the y direction, as illustrated in FIG. 4B. This phenomenon is believed to be explained by the anisotropic response of the M-hydrogel to tensile and compressive strain as previously discussed, i.e., movement in x direction exerts predominantly compressive strain which reduces resistance, whereas movement in y direction exerts predominantly tensile strain, which increases the resistance.

Figure 7A:
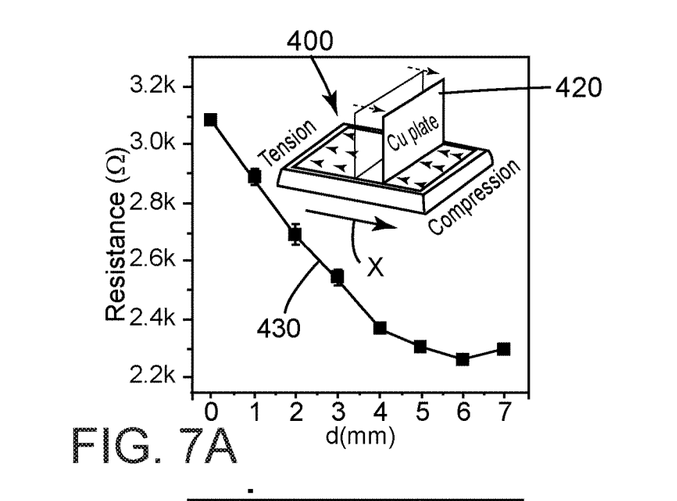
FIGS. 7A to 7D illustrate the motion direction sensing capability of the polymer composite material.

To test this explanation, the resistance change of a M-hydrogel sensor undergoing the same amount of tensile and compressive deformation has been measured with the set shown in FIG. 7A. When a conducting copper plate 420, which separates the M-hydrogel 400, moved to either side in the x direction, the resistance 430 of the M-hydrogel was reduced, which means that the motion in the x direction induces predominantly a compressive strain response.

Figure 7B:
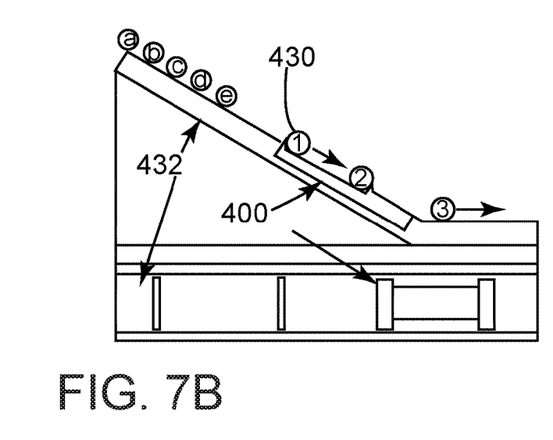

To test whether another relevant aspect of motions-speed can also be sensed by the M-hydrogel, a model experiment was conducted, in which a cylinder 430 was rolled down a slope having an M-hydrogel surface as illustrated in FIG. 7B. The slope was made of an eco-flex mold 432, which is a platinum-catalyzed silicone. The mean velocity of the cylinder 430 passing over the M-hydrogel surface 400 was controlled by the initial position of the object on the slope (i.e., the first position was at a first height indicated by "a," the second position was at a lower height indicated by "b," and so on). The cylinder 430 touches the first time the M-hydrogel sensor 400 at position 1, moves over the sensor as indicated by position 2, and escapes from the sensor at position 3.

Figure 7C:
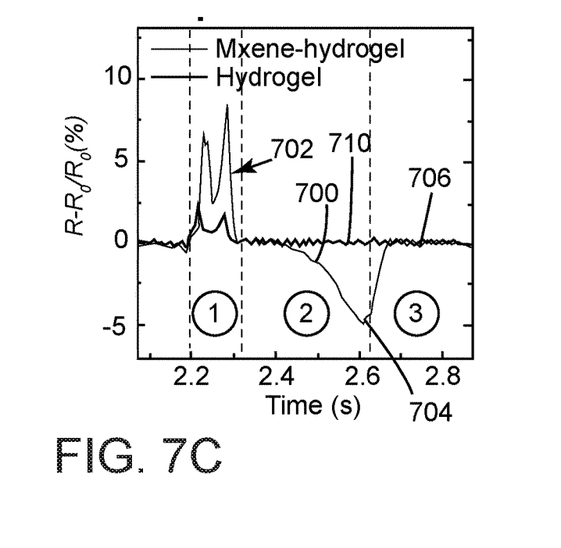

The measured fractional resistance change of the M-hydrogel sensor exhibits three distinguished regions while the cylinder was rolled down its surface, as shown in FIG. 7C. The fractional resistance change curve 700 first shows upward peaks 702, when the cylinder 430 reaches the M-hydrogel (region "1") in FIG. 7C. When the cylinder 430 arrives at region 2, the fractional resistance change curve shows a wide downward peak 704 as the velocity of the cylinder is higher than the relaxation rate of the M-hydrogel. When the cylinder 430 separates from the M-hydrogel sensor 400, the sensor goes to the initial resistance value 706 (region "3") due to the elastic property of the polymer composite material.

Figure 7D:
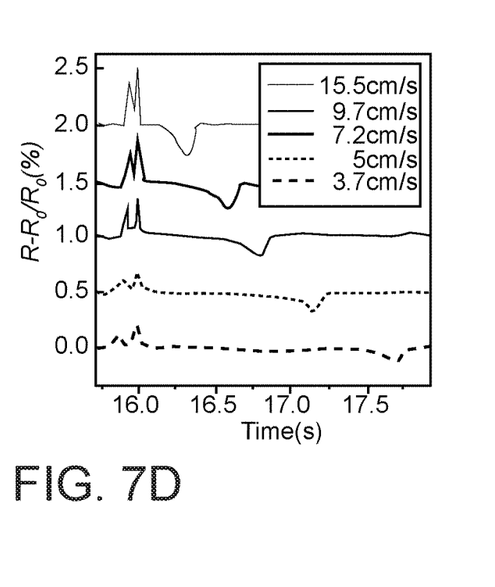

Repeating these experiments for different initial heights of the cylinder 430, as the mean velocity of the cylinder 430 increased, the maximum value of the peaks in both regions "1" and "2" are increasing, and the length of the region "2" decreases as illustrated in FIG. 7D. In comparison, a pristine hydrogel based sensor does not show any peaks in region "2," (see curve 710 in FIG. 7C), thus demonstrating the unique role of MXene in speed sensing.

The unique response of the M-hydrogel material and sensor to (1) motion speeds and (2) directions indicate the interesting and promising sensing capabilities endowed by the addition of MXene nanoflakes into the M-hydrogel system, especially for complex and subtle motions.

Given the above advantageous properties of the M-hydrogel material, it may be used as a sensing material to detect various bodily motions (hand gestures and facial expressions) and/or to monitor vital signals (pulse). It may also be used to demonstrate its potential in applications such as wearable electronics. Due to the unique soft, sticky, and stretchable characteristics, the M-hydrogel material can readily adhere to different spots on the human body with complex 3D geometry (hand, neck, face, etc.) without using adhesives.

Figure 8A:
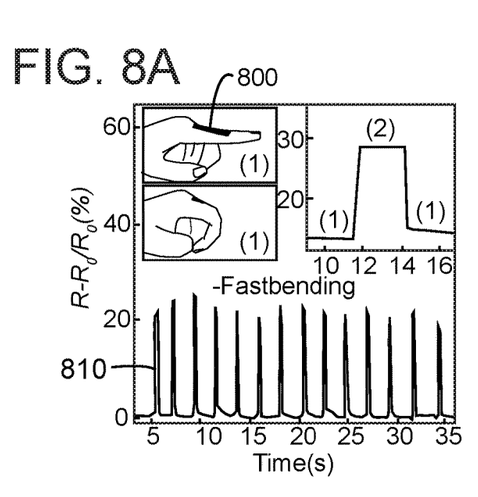
FIGS. 8A to 8E illustrate the response of the polymer composite material when applied to the human had or face.
Figure 8B:
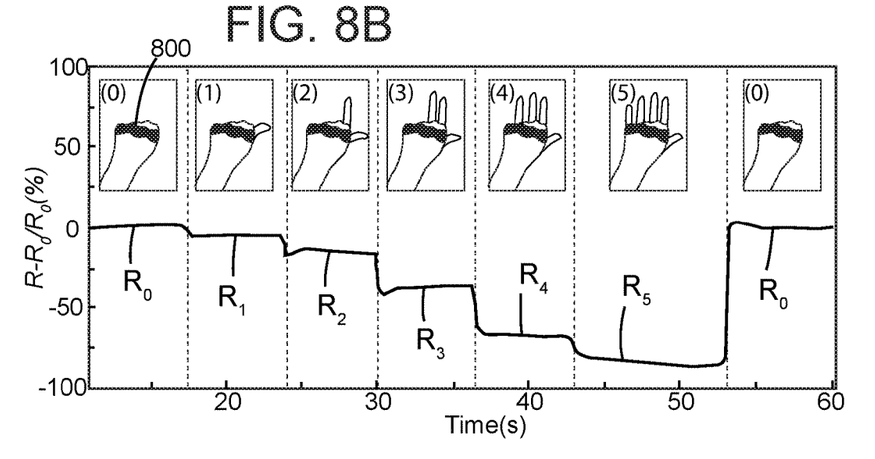

For example, the M-hydrogel material was attached to the index finger as illustrated in FIG. 8A. When the finger was bent by 90°, the M-hydrogel sensor 800 shown a 20% change in resistance as illustrated by curve 810 in FIG. 8A. The signal is clear and stable under both fast and slow bending motions (see also insert of FIG. 8A where "1" corresponds to a straight finger and "2" corresponds to a bent figure). More complex gestures involving full hand motion was readily detected by adhering the M-hydrogel sensor to the knuckle, as illustrated in FIG. 8B. The various gestures of "zero," "one," "two," "three," "four," and "five" each showed a distinct resistance value $R_0$ to $R_5$, as also illustrated in FIG. 8B. The signals were fully recoverable as also illustrated by the values of $R_0$ at time 0 and at 55 s.

Figure 8C:
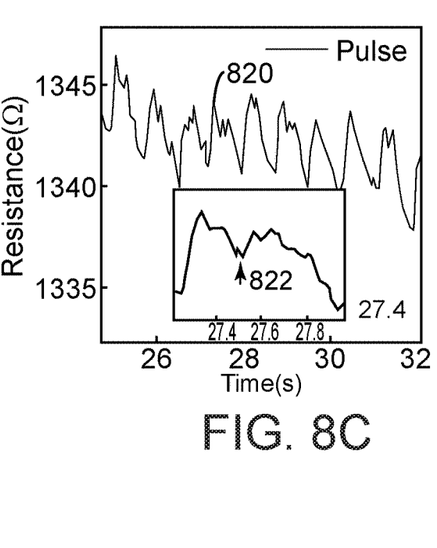
Figure 8D:
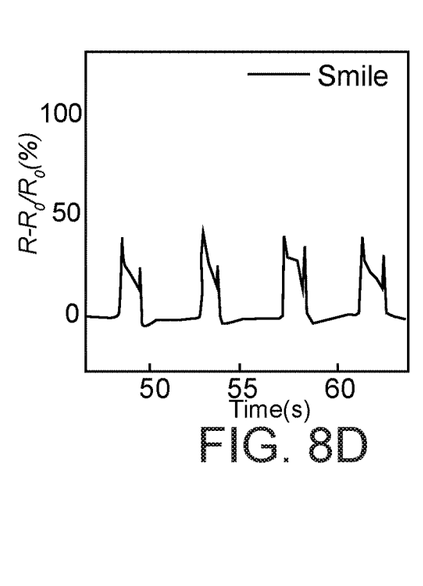
Figure 8E:
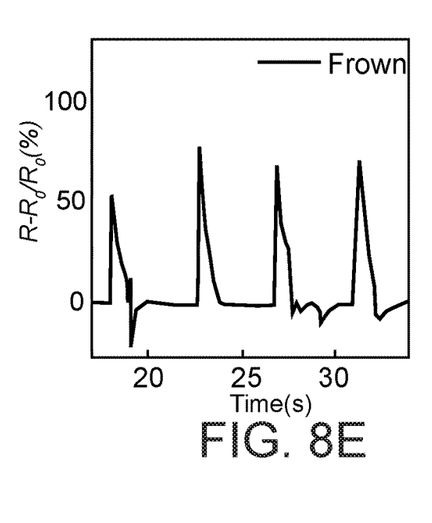

When the M-hydrogel sensor 800 has been mounted over the carotid artery, delicate waveforms 820 have been detected showing the pulse with the characteristic double peak and Dicrotic notch 822 along with other fingerprint signals allowing for accurate pulse monitoring, as illustrated in FIG. 8C. When the M-hydrogel sensor 800 has been adhered to the forearm, facial expressions such as smiling (see FIG. 8D) and frowning (see FIG. 8E) can be clearly distinguished.

The unique sensing capabilities discussed above with regard to the M-hydrogel material, i.e., capable of distinguishing motion-speed and direction inputs, open up the strain sensors having such materials to advanced sensing applications. Couple of these advances sensing applications are now discussed.

Figure 9A:
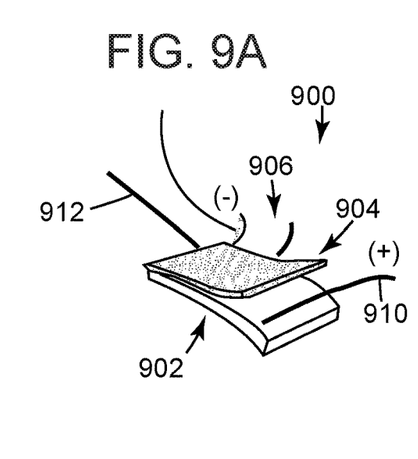
FIGS. 9A to 9D illustrate the response of the polymer composite material when used as a writing pad.
Figure 9B:
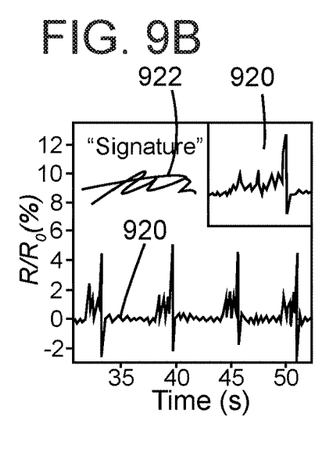

According to an embodiment, a M-hydrogel sensor 900 was used as a sensing pad for signature recognition. The M-hydrogel sensor 900 includes a base layer (e.g., eco-flex frame) 902, the M-hydrogel material 904, and a protection film (e.g., Polyethylene terephthalate (PET)) 906 formed over the M-hydrogel material 904, as illustrated in FIG. 9A. Two electrodes 908 and 910 are attached to the M-hydrogen material of the sensor for measuring an electrical signal associated with the fractional resistance change. A stick 912 is used to write on the sensor 900. Because individual handwriting involves a set of unique characteristics which include force, writing speed, writing sequence, etc., the M-hydrogel sensor shows in FIG. 9B complex and unique waveforms 920 for even a simple signature 922.

Figure 9C:
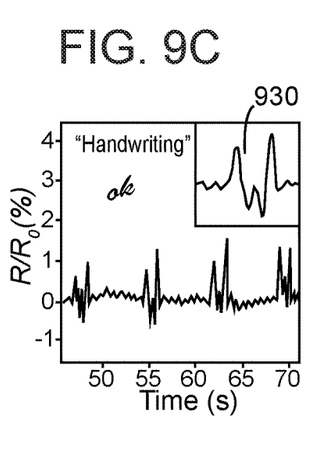
Figure 9D:
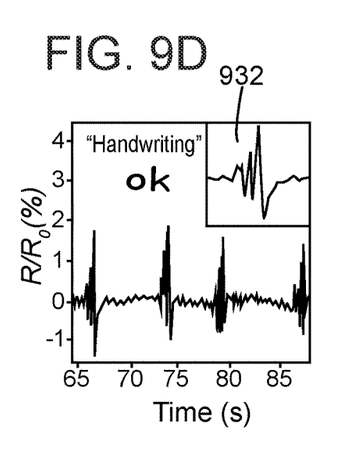

Even a simple word like "OK," when written by two different persons, show significantly different waveforms 930 and 932 in FIGS. 9C and 9D, respectively. This means that the M-hydrogel sensor 900 is capable to distinguish the handwriting of various persons, which indicates the great potential of the M-hydrogel sensor in anti-counterfeiting applications.

Figure 10A:
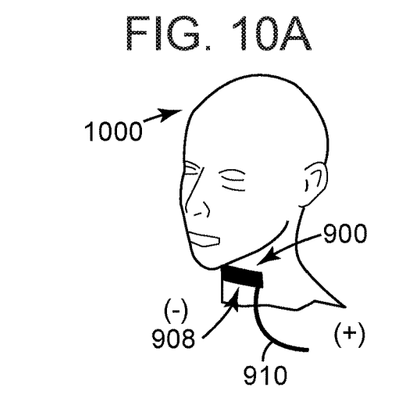
FIGS. 10A to 10D illustrate the response of the polymer composite material when used to recognize sounds.
Figure 10B:
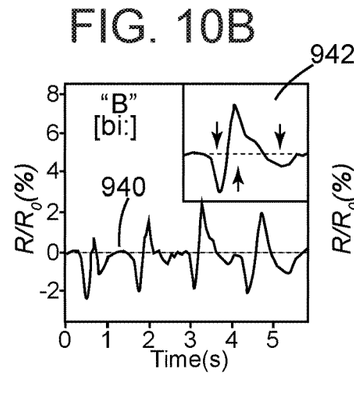
Figure 10C:
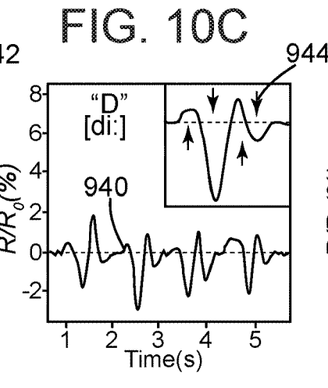
Figure 10D:
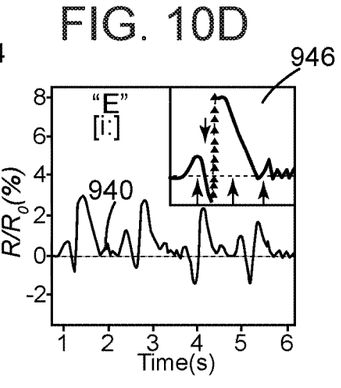

The M-hydrogel sensor 900 was further used to detect a vital signal, which urgently requires accurate monitoring, i.e., the phonatory process (voicing). When attached to the laryngeal prominence (Adam's apple) of a person 1000, as illustrated in FIG. 10A, the M-hydrogel sensor 900 exhibits stable and unique patterns 940 for the voices of the test subject. As shown in FIGS. 10B-10D, even similarly sounding single syllables such as "B", "D", "E" produce easily distinguishable patterns 942, 944, and 946, respectively, which are significantly better than the patterns from previous reports.

Figure 11A:
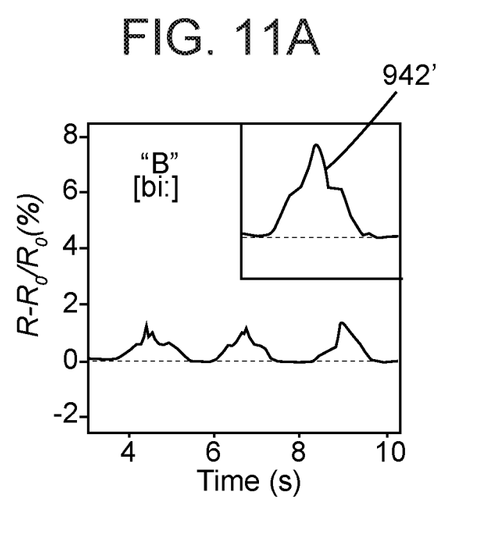
Figure 11B:
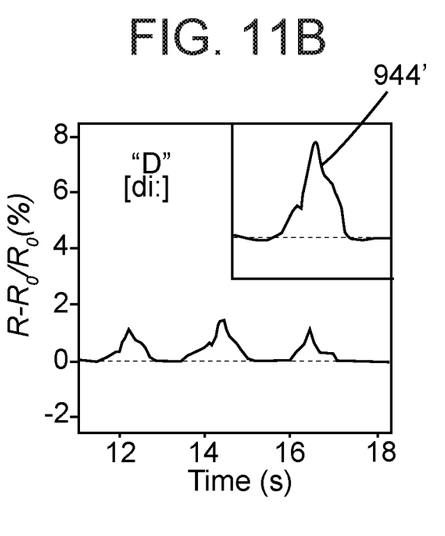
Figure 11C:
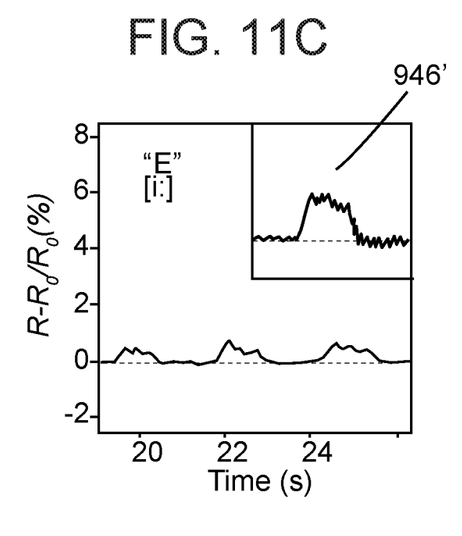

For comparison, FIGS. 11A to 110 show corresponding patterns 942', 944' and 946' obtained for the same syllables and the same person with a sensor that includes pristine hydrogel. One will note that the patterns 942', 944' and 946' for the pristine hydrogel resemble to each other, which would make a device to not be able to distinguish between these three syllables. This difference is due to the sensitivity of the M-hydrogel material towards both the strength and frequency of subtle vibrations (the characteristics discussed with regard to FIGS. 4A and 4B) related to the laryngeal prominence and surrounding skin. The impressive sensing capability of the M-hydrogel sensor 900 on phonation via the electromechanical approach suggests the great promise for us to "hear" the vocally impaired.

Interestingly, the viscoelastic polymer based strain sensor 900 is strong in recognizing human vocal sounds through mechanical motions of a human larynx, which clearly show distinguishable and stable signals. In most of the existing vocal sensing strain sensors, a single syllable is presented as a single peak, thus it is very hard to recognize different sounds with same number of syllables. However, the vocalization of humans is based on complicated motions of the vocal organs even for making only a single syllable. This means that if a strain sensor can catch the fine movements in vocal organs, it can significantly increase the accuracy and reliability of vocal recognition. The above measurements have shown that the strain sensor 900 based on the novel viscoelastic polymer composite material can clearly identify patterns due to fractional resistance change from single syllable sounds.

One or more of the embodiments discussed above are directed to a novel multimodal resistive strain sensor, which is based on a composition of conductive nanofillers and viscoelastic hydrogel, where the amount of nanofillers may be about 0.1 to 5% by weight. This composition has been shown above to be able to sense strains caused by motions such as bending, stretching and compression, and can also detect various subtle details of motions such as directions and velocities. The conductive nanofillers may include, in addition or instead of MXenes (other MXene type carbides/carbonitrides), graphene (hydrophilic treated) and graphene oxides, carbon nanotubes, and other conductive fillers with hydrophilic surface properties. In one application, the viscoelastic hydrogel can be extended to any synthetic hydrogels such as those based on Poly (vinyl alcohol) (PVA), Polyethylene glycol (PEG), Poly (2-hydroxyethyl methacrylate) (PHEMA), etc.

The hydrogel composite material discussed herein is also effective in detecting human vocal sound and individual handwriting, accurately and stably. It can be used in medical settings as sensitive probe for EKG machines, hear monitors, pulse monitors, and even irregular breathing patterns.

The sensors discussed above can be fixed to the desired object to be investigated without any adhesion layers such as glues or tapes. However, one skilled in the art would understand that these sensors can also be attached with glues or tapes or other means. One desirable function exhibited by the sensors discussed above is detection of local deformations, caused by various motions at the viscoelastic surface of the polymer composite sensor. In response to different applied force and strain rate, the viscoelastic materials can show both elastic and viscous deformations. It means that the viscoelastic materials experience a more varied range of deformations from mechanical movements than the elastic materials. These effects are very useful when a stress is locally focused on the surface of the sensor by shape transformation or by local motion of the objects. For example, if the target object is moving over the sensor, clearly distinguishable traces caused by movements of the object at the viscoelastic surface can be observed. Moreover, these traces can make additional deformations on the surface of the polymer composite material in real time. Furthermore, these deformations are very sensitive to the details of motions (such as moving directions and/or velocity changing).

A strain sensor that embeds one or more properties discussed above is now discussed with regard to FIG. 12. Strain sensor 1200 includes a base layer 1202. The base layer 1202 can be made of an eco-flex mold. Those skilled in the art would understand that the base layer may be made of any flexible and malleable material that allows a movement to be monitored in a subject. The base layer, if present, should be so elastic to propagate the detected movement to the next layer of the sensor.

Figure 12:
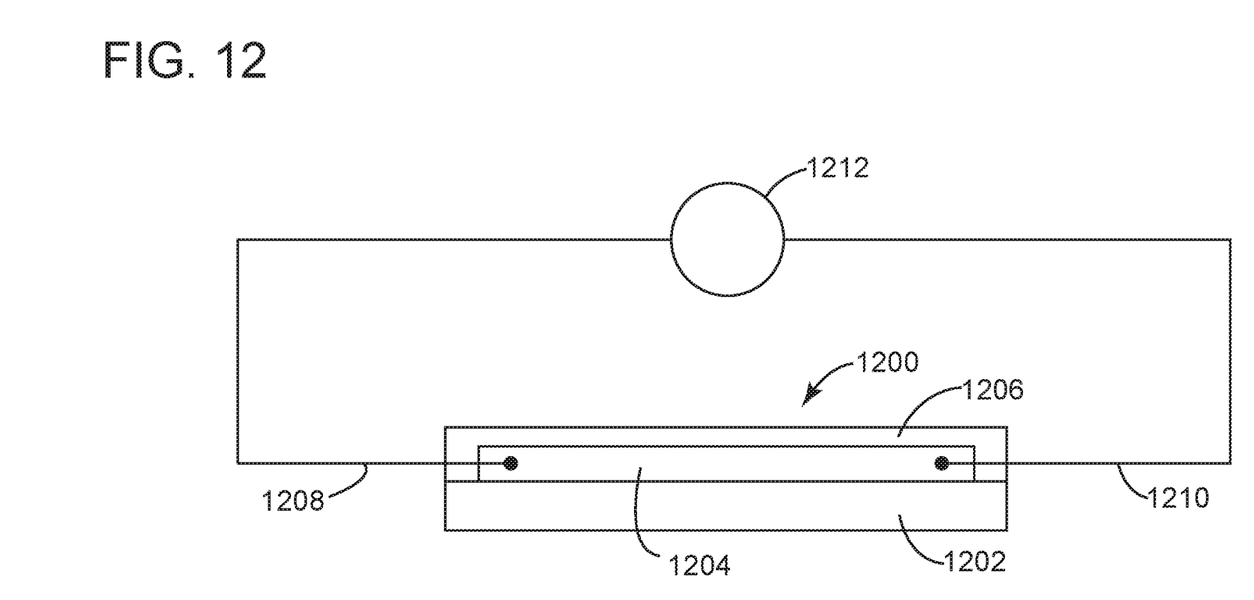
FIG. 12 illustrates a strain sensor that uses the polymer composite material.

On top of the base layer 1202, a viscoelastic conductive material is formed as a sensing layer 1204. The viscoelastic conductive material shows both elastic and viscous deformations. This material is made of a composition of conductive nanofillers and viscoelastic hydrogel. In one application, the composition includes electrically conductive nanolayers of MXenes distributed randomly inside a viscoelastic hydrogel. The combination of MXenes and hydrogel is called herein M-hydrogel. In one application, the sensing layer is made of a combination of transition metal carbides, nitrides or carbonitrides and a hydrogel.

Optionally, for protection, a protective film 1206 may be formed in top of the sensing layer 1204. The protective layer may be made of PET, which is flexible enough to allow a deformation or compression or strain exerted on it to propagate to the sensing layer 1204. The protective film may be added to protect the sensing layer from humidity, impurities, and other exterior conditions.

Two electrodes 1208 and 1210 may be connected to the sensing layer 1204 for sensing a change in the fractional resistance change of the layer. These two electrodes may then be connected to a sensing device 1212 for translating the fractional resistance change into a desired signal, e.g., a change in voltage, in current, in a sound, etc. The sensing device 1212 may be a processor, a computer, a smartphone, an integrated circuit, a traditional electric circuit, etc.

Figure 13:
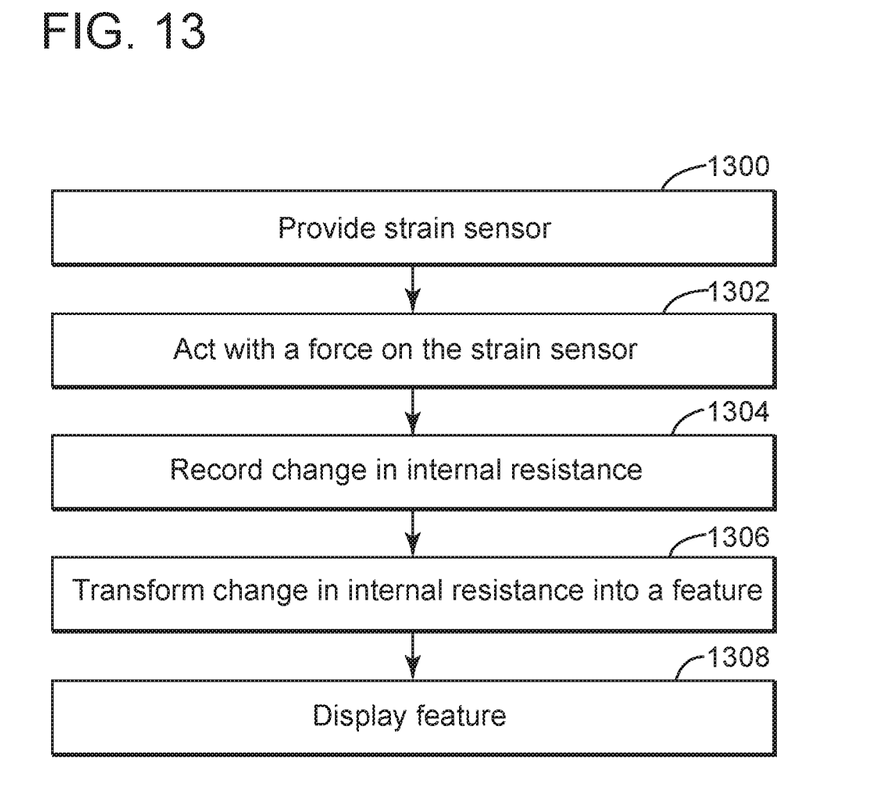
FIG. 13 is a flowchart of a method for determining with a strain sensor a feature associated with the act of applying the strain to the strain sensor.

The strain sensor 1200 may be used as now discussed with regard to FIG. 13. In step 1300, the strain sensor is provided at a location where data is desired to be obtained. For example, the strain sensor may be placed on human skin for pulse measurements or heart signals detection or face recognition. Alternatively, the strain sensor may be placed on a hard surface and then various forces (writing) are exerted on it.

In step 1302, the strain sensor is impacted by a force (strain or stress or any type of force) generated by the object to be investigated. The strain sensor transforms this external force into an internal fractional resistance change, which is recorded in step 1304 by a sensing device 1212. The sensing device 1212 may apply various known processes and/or algorithms for transforming in step 1306 the fractional resistance change into a feature, which may be, for example, writing, electrical signal representative of a sound, representation of heart beat, image, etc. In step 1308, the method may display such feature as an image on a screen or as a sound with a loudspeaker. Those skilled in the art would understand that the list of applications of the strain sensor 1200 discussed herein is not exhaustive and many other applications may be imagined, like, detecting underwater sounds associated with various mammals, detecting seismic signals, etc.

Figure 14:
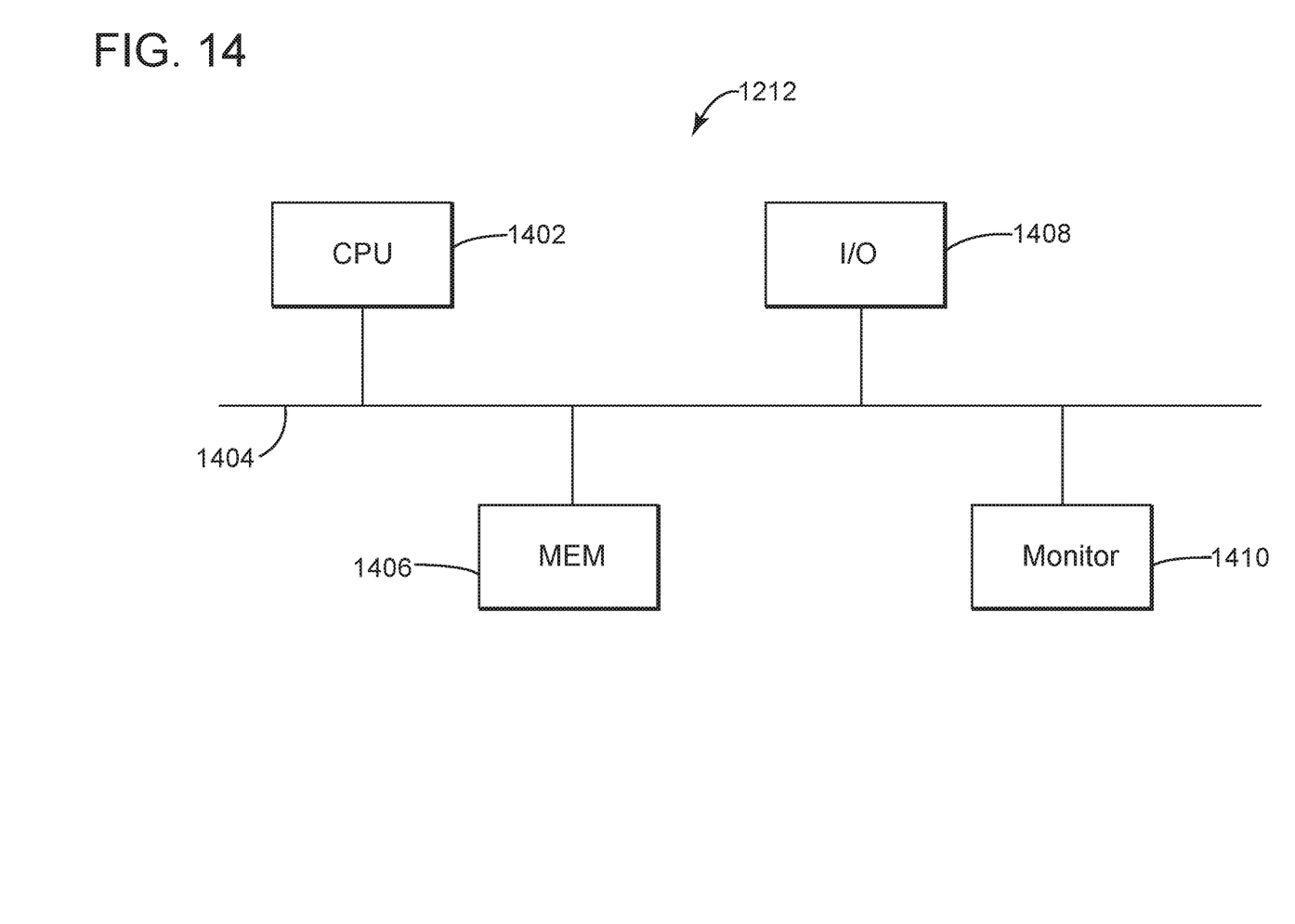
FIG. 14 is a schematic illustration of a sensing device.

The sensing device 1212 may be implemented in a computing device. The computing device is illustrated in FIG. 14. The computing device 1212 includes a processor 1402 that is connected through a bus 1404 to a storage device 1406. Computing device 1212 may also include an input/output interface 1408 through which data can be exchanged with the processor and/or storage device. For example, a keyboard, mouse, a wireless device or other device may be connected to the input/output interface 1408 to send commands to the processor and/or to collect data stored in storage device or to provide data necessary to the processor. Results of this or another algorithm may be visualized on a screen 1410 or reproduced with a loudspeaker.

The disclosed embodiments provide methods and devices for measuring a strain. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A viscoelastic strain sensor comprising:
a sensing layer including a viscoelastic material,
the viscoelastic material including a viscoelastic hydrogel and a conductive nanofiller,
wherein the viscoelastic material has a fractional resistance change that increases with an increase of an applied tensile strain, and
wherein the viscoelastic material has a fractional resistance change that decreases with an applied compressional strain.

2. The sensor of claim 1, wherein the fractional resistance change under compressive strains is higher than under tensile strains.

3. The sensor of claim 1, further comprising:
a base layer on which the sensing layer is formed; and
a protection layer that covers the sensing layer.

4. The sensor of claim 1, wherein the conductive nanofiller includes MXene.

5. The sensor of claim 1, wherein the conductive nanofiller includes MXene nanosheets.

6. The sensor of claim 5, wherein the nanosheets are randomly distributed inside the viscoelastic hydrogel.

7. The sensor of claim 1, wherein a weight by percentage of the conductive nanofiller relative to a total weight of the viscoelastic material is larger than zero and smaller than 4.

8. The sensor of claim 1, wherein the sensing layer is malleable.

9. The sensor of claim 1, wherein the fractional resistance change is associated with a direction of the strain applied to the sensing layer.

10. The sensor of claim 1, wherein the fractional resistance change is associated with a speed of an object that applies the strain to the sensing layer.

11. The sensor of claim 1, wherein the fractional resistance change is associated with a pulse applied by an object to the sensing layer.

12. A method for determining a strain with a strain sensor, the method comprising:
providing a sensing layer of the strain sensor;
applying the strain to the sensing layer;
measuring a fractional resistance change of the sensing layer due to the applied strain; and
transforming the measured fractional resistance change into a feature that characterizes the applied strain,
wherein the sensing layer includes a viscoelastic hydrogel and a conductive nanofiller,
wherein the viscoelastic material has the fractional resistance change that increases with an increase of an applied tensile strain, and
wherein the viscoelastic material has a fractional resistance change that decreases with an applied compressional strain.

13. The method of claim 12, further comprising:
sticking the sensing layer directly on human skin.

14. The method of claim 12, wherein the conductive nanofiller includes MXene.

15. The method of claim 12, wherein the conductive nanofiller includes MXene nanosheets.

16. The method of claim 15, wherein the nanosheets are randomly distributed inside the viscoelastic hydrogel.

17. The method of claim 12, wherein a weight by percentage of the conductive nanofiller relative to a total weight of the viscoelastic material is larger than zero and smaller than 4.

18. The method of claim 12, wherein the fractional resistance change is associated with a direction of the strain applied to the sensing layer or the fractional resistance change is associated with a speed of an object that applies the strain to the sensing layer.

19. The method of claim 12, wherein the fractional resistance change under compressive strains is higher than under tensile strains.

20. The method of claim 12, wherein the fractional resistance change is associated with a pulse applied by an object to the sensing layer.

21. The method of claim 12, wherein the feature is a facial expression, a writing, or a sound.

22. A viscoelastic material comprising:
a viscoelastic hydrogel; and
a conductive nanofiller,
wherein the viscoelastic material has a fractional resistance change that increases with an increase of an applied tensile strain, and
wherein the fractional resistance change decreases with an applied compressional strain, and
wherein the fractional resistance change under compressive strains is higher than under tensile strains.

23. The viscoelastic material of claim 22, wherein the conductive nanofiller is MXene.

24. The viscoelastic material of claim 22, wherein a weight by percentage of the conductive nanofiller relative to a total weight is larger than zero and smaller than 4.

* * * * *